Figure 1:
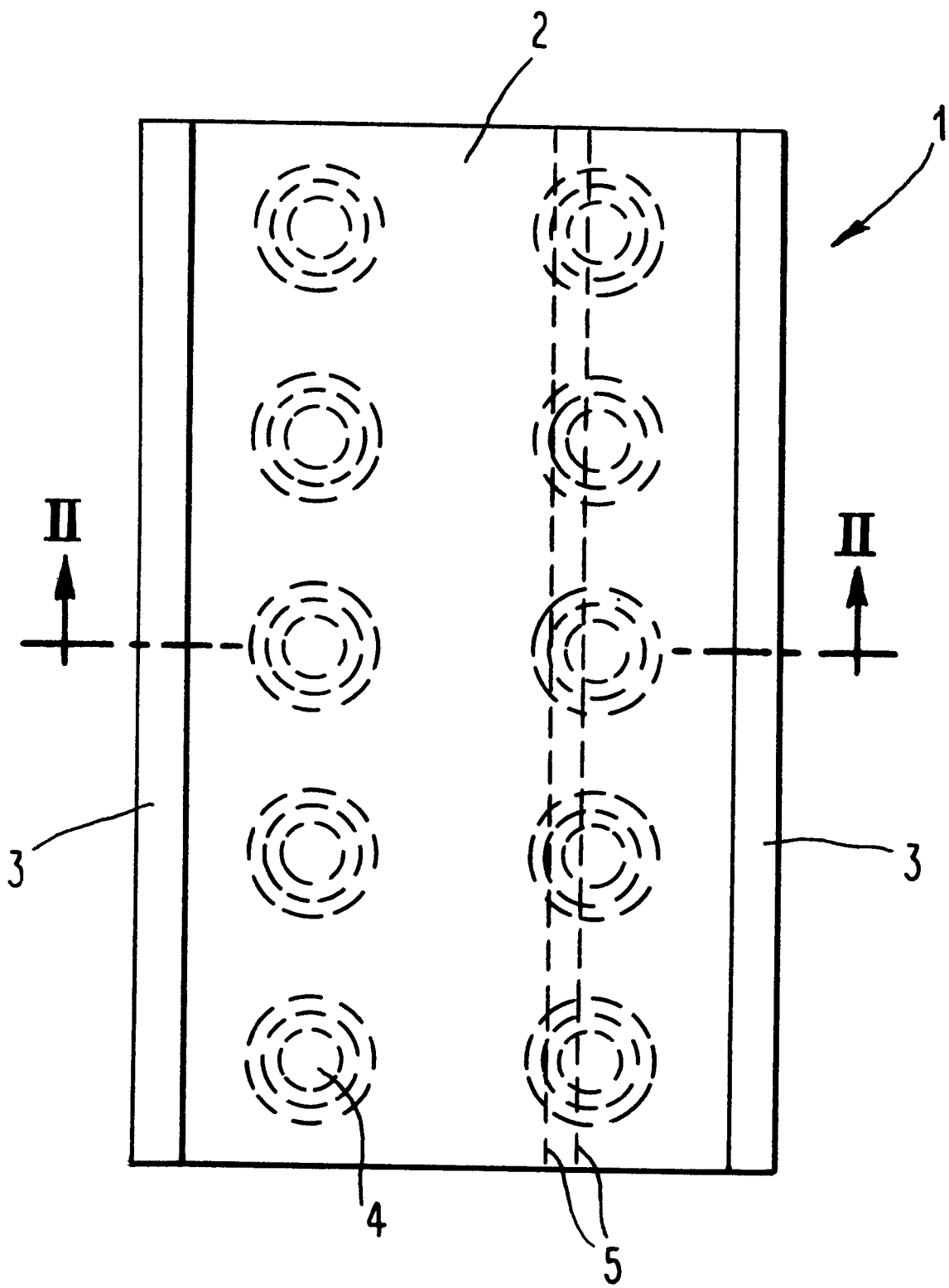

United States Patent [19]
Anhäuser et al.

[11] Patent Number: 6,142,954
[45] Date of Patent: Nov. 7, 2000

[54] EPICUTANEOUS TEST PLASTER

[75] Inventors: Dieter Anhäuser, Melsbach; Jürgen Ecker, Neuwied; Heike Schentek, Kurtscheid, all of Germany

[73] Assignee: Lohmann GmbH & Co. KG, Neuwied, Germany

[21] Appl. No.: 09/319,744

[22] PCT Filed: Nov. 21, 1997

[86] PCT No.: PCT/EP97/06532

§ 371 Date: Jul. 15, 1999

§ 102(e) Date: Jul. 15, 1999

[87] PCT Pub. No.: WO98/25521

PCT Pub. Date: Jun. 18, 1998

[30] Foreign Application Priority Data

Dec. 11, 1996 [DE] Germany .................. 296 21 365 U

[51] Int. Cl.[7] .................................................. A61B 5/00
[52] U.S. Cl. ...................... 600/556; 600/584; 604/304
[58] Field of Search ........................... 600/556, 557, 600/584; 604/304, 307

[56] References Cited

U.S. PATENT DOCUMENTS

| | | | |
|---|---|---|---|
| 2,841,138 | 7/1958 | Laub | 600/556 |
| 4,788,971 | 12/1988 | Quisno | 600/556 |
| 5,044,372 | 9/1991 | Anhauser et al. | 600/556 |
| 5,325,864 | 7/1994 | Gerber | 600/556 |

FOREIGN PATENT DOCUMENTS

| | | |
|---|---|---|
| 3810658C2 | 1/1991 | Germany . |
| 4328112C1 | 12/1994 | Germany . |
| WO 94/17735 A1 | 8/1994 | WIPO . |

*Primary Examiner*—Cary O'Connor
*Assistant Examiner*—Pam Wingood
*Attorney, Agent, or Firm*—Law Offices of Jane Massey Licata

[57] ABSTRACT

A patch test plaster having at least one active substance receptacle arranged on a backing film, having a highly elastic backing film which is made of polymeric material, is impermeable to liquid water but permeable to water vapour, and is releasibly connected on the surface facing away from the skin to a supporting sheet and is provided on the surface facing the skin with an adhesive layer which is in turn covered by an at least two-part detachable protecting layer before application of the plaster, is characterized in that the protecting layer has a hinge-like connection on two opposite edges to the supporting sheet.

8 Claims, 2 Drawing Sheets

EPICUTANEOUS TEST PLASTER

The invention relates to an application aid for patch test plasters having at least one active substance receptacle arranged on a backing surface.

Patch test plasters are used in patch tests which serve, in particular, to identify the causes of allergic contact dermatitis. For this purpose, the test substance is applied to a test plaster which is then applied to selected areas of the patient's skin. After a predetermined period, the test plaster is removed.

The first reading of the patient's reaction to exposure to the active substance takes place immediately after removal of the test plaster; further readings are taken where appropriate at particular time intervals. It is moreover helpful to be able to mark the test site on the skin, so that the skin contacted with the test substance can be found again reliably.

The structure of patch test plasters is in principle as follows: absorbent flat materials, for example made of woven or nonwoven textiles, or containers which are open towards the skin are arranged as active substance receptacles on an adhesive backing layer or are formed in the backing substance itself.

The area of the test plaster which is to be brought into contact with the skin is covered by a detachable protecting layer before application. To date, flat textile materials such as, for example, woven or nonwoven fabrics, and polymers or metal foils, have been proposed as backing layer. A considerable disadvantage of known patch test plasters has been that the flexibility of the backing materials was too low to prevent premature detachment of the test plaster from the skin due to unavoidable body movements. To eliminate this disadvantage, DE-C 38 10 658 proposes a backing material made of a thin, highly elastic polymer film which is impermeable to liquid water but permeable to water vapour and whose ease of handling is ensured by attaching a redetachable, relatively stiff supporting sheet to the backing film surface facing away from the skin. The supporting sheet is removed after application.

However, despite this advance, the ease of handling of such test plasters has not to date been entirely satisfactory. On application it must be possible to grasp the plaster while avoiding contamination of the adhesive layer, including, of course, the active substance receptacles. It must also be possible to remove the supporting sheet conveniently after the plaster has been stuck on. Although assistance can be provided here by a supporting sheet projecting beyond the backing layer, this requires increased material and additional and/or complicated steps during production.

It is therefore an object of the invention to produce a patch test plaster which, while having good conformability, features acceptable ease of handling which can be achieved with justifiable means.

The achievement of this object has surprisingly been found in the case of a patch plaster having at least one active substance receptacle arranged on a backing layer, having a highly elastic backing film made of polymeric material which is impermeable to liquid water but permeable to water vapour and which is releasibly connected on the surface facing away from the skin to a supporting sheet and is provided on the surface facing the skin with an adhesive layer which is in turn covered by an at least two-part detachable protecting layer before application of the plaster, in that the protecting layer has hinge-like connection on two opposite edges to a supporting sheet.

This construction allows, inter alia, the supporting sheet to have the same surface area as the backing film, and thus additional cutting and/or punching steps to be avoided. The protecting layer parts can be swung outwards after detachment from the adhesive layer and can be grasped for application of the plaster without having to take into account contamination of the adhesive layer. After the plaster has been pressed onto the skin, the supporting sheet with the attached parts of the protecting layer can be removed without difficulty.

Another advantage of the invention is that it is possible, after the protecting layer parts have been swung open, to charge the active substance receptacles with the substances to be tested, and the receptacles are protected from external influences up to the time of application by swinging the protecting layer parts back into the initial position.

There are numerous possibilities for producing the hinge-like connection between protecting layer and supporting sheet, and some of those which are particularly preferred will be described. On the one hand, the protecting layer can project in the form of a strip beyond the edge of the plaster and is, after folding round this edge, fastened adhesively on the surface of the supporting sheet facing away from the skin. A crease line in the protecting layer promotes moveability thereof around the hinge axis. The converse construction, i.e. the projecting supporting sheet being fastened, on the underside of the protecting layer, after folding round the edge, is also possible in principle but will remain restricted to special cases because of the possible disadvantages. In the event that circumstances allow the supporting sheet and the protecting layer to be produced from the same material, a continuous flat material is folded around the backing surface to allow the ends to come to rest on the adhesive layer side. Adhesion of the backing film to this flat material is produced by known methods described in detail hereinafter.

In another preferred embodiment of the invention, the supporting sheet, adhesive-coated backing film and protecting layer have the same outer contours and the hinge-like connection between protecting layer and supporting sheet is formed by attaching a strip which is creased longitudinally, with one part adhering to the side of the supporting sheet facing away from the skin and the other part adhering to the free side of the protecting layer. The strip is preferably provided with a pressure sensitive adhesive, but can also be fixed by other adhesive systems. Sealing on at room temperature or with input of heat provides other possibilities for fixing. It is, of course, unnecessary for the strip to enclose the entire length of the edge of the hinge; on the contrary, it suffices in some cases if only parts of the edge are covered.

The patch test plaster according to the invention preferably has a quadrangular contour with the hinge-like connections being formed on opposite edges, preferably the long edges. The size of the backing film does not correspond to the size of the supporting sheet if a marking strip which is adhesive on the skin side and is releasibly fastened on the surface facing away from the skin to the supporting sheet which projects beyond the backing film is arranged parallel to at least one edge of the plaster. After application of the plaster, this strip adheres beside the latter to the skin and makes it possible to make markings related to the test site.

Suitable materials for the supporting sheet are known polymers such as, for example, polyethylene, polypropylene, polyamide or polyester. However, textile flat. materials and paper are also in use. The thickness of the supporting sheet varies between 30 and 200 Wm, preferably 30–80 μm. The supporting sheet is bonded to the backing film with a suitable adhesive, or the connection is brought about by those mechanical adhesive forces which arise when the backing film is produced by extrusion, casting or another known method for producing films directly on the supporting sheet.

The backing film is opaque or transparent and can be produced by known techniques from known raw materials. Transparent films are preferred because they permit observation of the test plasters during application. The best results in this regard are obtained when the active substance receptacles are also made transparent in addition. Examples of raw materials for the backing film which may be mentioned are: polyurethanes, polyvinyl chlorides, polyvinylidene chlorides, polyvinyl alcohols, polyacrylates, polysulphones, polystyrenes, polyethylene, polypropylene, polyamides, ethylene/vinyl acetate copolymers, polyesters, polycarbonates, polyvinyl fluoride and other fluorine-containing polymers. Backing films based on polyurethane are particularly preferred. The thickness of suitable films is generally in the region of 7–120 $\mu$m, preferably of 15–50 $\mu$m. The water vapour permeability should be at least 300 $gxm^{-2} \times 24h^{-1}$.

The adhesive layer can consist of known physiologically acceptable materials. Examples which may be mentioned are rubber, rubber-like synthetic homopolymers, copolymers or block polymers, polyacrylates and corresponding copolymers, polyurethanes and silicones. The amount of the adhesive applied per unit area is between 15 and 80 $g/m^2$, preferably 30–50 $g/m^2$.

The material for the protecting layer can be that which is also used for the supporting sheet. However, it is also possible to employ, for example, polytetra-fluoroethylene, cellophane, polyvinyl chloride, abhesively treated papers, metal foils and polymer-coated metal foils. The weights per unit area are 30–250 $g/m^2$, preferably 50–150 $g/m^2$. The protecting layer side which is in contact with the adhesive layer must allow redetachment with a force which is less than that for detaching the supporting sheet from the backing film. The ends of the at least two-part protecting layer which come to rest on the adhesive layer are most expediently provided with grasping aids in a usual manner.

The active substance receptacles are circular, angular, oval or designed in any other two-dimensional shape, and usually consist of absorbent material such as, for example, paper, nonwoven or woven fabrics or gel-like polymers able to release the active substance to the skin. Dish-like devices are also used to receive the active substances. The use of cellophane or polyvinyl alcohol polymers have proved suitable for producing transparent receptacles. In general, the active substance receptacles are fastened to the adhesive layer in a manner known per se. In order to prevent unintended migration of liquid test substances from the receptacle, it is possible to provide an encircling film which covers the receptacle with about half its width and is fastened with the other half of its width to the adhesive layer, without impairing the intended skin contact area of the active substance receptacle.

The patch test plasters according to the invention can be designed as single plasters, that is to say with only one active substance receptacle, but preferably have a plurality of active substance receptacles arranged in accordance with a predetermined geometric pattern, preferably in row form. The row or, if required, two or more parallel rows extend in the axial direction of the plaster. Intended break lines can be provided between the individual receptacles to make it possible easily to detach one plaster with the required number of receptacles from a longer plaster web.

The invention is explained further by means of figures. They are not drawn true to scale, and the thickness of the layers present is exaggerated to improve clarity. Identical elements have the same reference numbers.

These show:

FIG. 1 a view of a patch test plaster according to the invention

Figure 2:
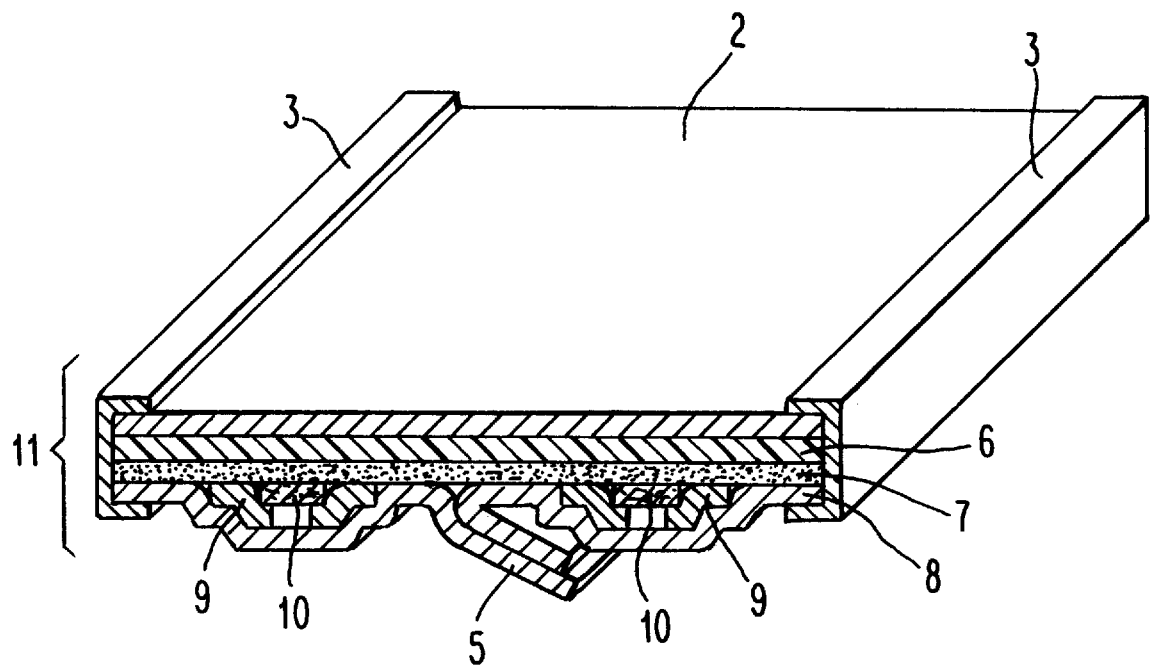
Figure 3:
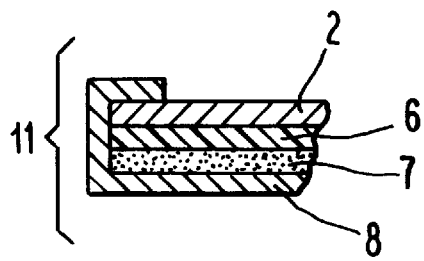

FIGS. 2 and 3 a cross section along line II/II in FIG. 1 and

Figure 4:
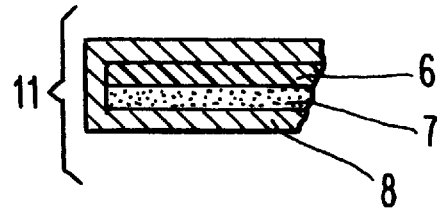

FIGS. 3 and 4 each a part of a cross section with various designs of hinge.

The patch test plaster in FIG. 1 is labelled with 1. It is viewed from above so that, of the layers forming the plaster, only the supporting sheet 2 can be seen. It is covered on opposite edges in each case by a strip 3 which forms the hinge-like connection to the protecting layer. The broken circles 4 indicate the points where the active substance receiving devices are attached on the underside of the plaster. In the present case there are arranged two parallel rows each of five devices. The broken lines 5 mark the course of the parts of the protecting layer which are designed with the grasping aid, on the opposite side of the plaster.

FIG. 2 shows a perspective view of a patch test plaster according to the invention in cross section along lines II/II in FIG. 1. The highly elastic backing film 6 is covered on the side facing away from the skin by the supporting sheet 2 of the same size. An adhesive layer 7 on which are fastened the active substance receiving devices consisting of a ring 9 with absorbent material 10 is arranged on the side of the backing film 6 facing the skin. The protecting layer is indicated by a 8, with the grasping aid 5 for the two parts thereof being evident.

Further possibilities for forming the hinge 11 are shown in FIGS. 3 and 4. It is evident from the parts of cross sections that in FIG. 3 the protecting layer 8 itself forms the hinge material and is fastened to the upper side of the supporting sheet 2 after wrapping around the edge. In FIG. 4, the protecting layer 8 and supporting sheet consist of a uniform material and therefore allow the required hinge-like connection 11 to be produced between the outer layers of the plaster by simply folding over the edges.

What is claimed is:

1. Patch test plaster for a human or animal body comprising an active substance receptacle arranged on a backing film which is made of a polymeric material, is impermeable to liquid water but permeable to water vapor and is releasably connected, on the surface facing way from the skin of the human or animal body, to a supporting sheet and is provided on the surface facing the skin of the human or animal body with an adhesive layer which is covered by an at least two-part detachable protecting layer which has a hinge-like connection on two opposite edges to the supporting sheet, said connection being formed by a strip which is stuck or sealed on, wherein said strip is longitudinally creased and encloses the edges.

2. Patch test plaster of claim 1, wherein the strip which forms the connection between the protecting layer and the supporting sheet projects beyond the edge of the plaster, of the protecting layer along a crease line on the surface of the supporting sheet facing away from the skin of the human or animal body.

3. The patch test plaster of claim 1, wherein the strip is sealed on.

4. The patch test plaster of claim 1, wherein the strip is divided into mutually separate sections over the length of the edge of the plaster.

5. The patch test plaster of claim 1, further comprising in an axial direction a row of active substance receptacles.

6. The patch test plaster of claim 5, comprising in an axial direction at least two parallel rows of active substance receptacles.

7. The patch test plaster of claim 1, wherein the backing film has smaller dimensions than the supporting sheet.

8. The patch test plaster of claim 7, further comprising a marking strip which is adhesive on the side facing the skin of the human or animal body and is releasably fastened on the surface facing away from the skin of the human or animal body to the supporting sheet which projects beyond the backing film and is arranged parallel to at least one edge of the plaster.

* * * * *